US012599693B2

(12) United States Patent
Mukhopadhyay et al.

(10) Patent No.: US 12,599,693 B2
(45) Date of Patent: Apr. 14, 2026

(54) AUGMENTED THERMOSET POLYMER SPONGES FOR IN SITU HEMOSTATIC TREATMENT OF EXTERNAL AND INTERNAL WOUNDS

(71) Applicant: UNIVERSITY OF CENTRAL FLORIDA RESEARCH FOUNDATION, INC., Orlando, FL (US)

(72) Inventors: Kausik Mukhopadhyay, Orlando, FL (US); Pritha Sarkar, Orlando, FL (US)

(73) Assignee: UNIVERSITY OF CENTRAL FLORIDA RESEARCH FOUNDATION, INC., Orlando, FL (US)

( * ) Notice: Subject to any disclaimer, the term of this patent is extended or adjusted under 35 U.S.C. 154(b) by 0 days.

(21) Appl. No.: 18/402,614

(22) Filed: Jan. 2, 2024

(65) Prior Publication Data

US 2024/0238472 A1    Jul. 18, 2024

(51) Int. Cl.
*A61L 15/26*        (2006.01)
*A61F 13/00*        (2024.01)

(52) U.S. Cl.
CPC ..... *A61L 15/26* (2013.01); *A61F 2013/00634* (2013.01); *A61L 2400/04* (2013.01)

(58) Field of Classification Search
CPC .............. A61L 24/001; A61L 24/0015; A61L 24/0089; A61L 2300/06; A61L 2300/11; A61L 2300/404; A61L 2400/04
See application file for complete search history.

(56) References Cited

U.S. PATENT DOCUMENTS 7,226,615 B2    6/2007  Yuksel et al.
8,999,377 B2    4/2015  Rolfes et al.
(Continued)

FOREIGN PATENT DOCUMENTS

EP        0287609 B1 *  3/1992    ............. A61B 5/416
EP        0948559 A1    3/2002
WO    2014035245 A1    3/2014

OTHER PUBLICATIONS

Beaman, Henry T. et al., "Hemostatic shape memory polymer foams with improved survival in a lethal traumatic hemorrhage model", Acta Biomaterialia, 137 (2022) 112-123.
(Continued)

*Primary Examiner* — Kim M Lewis
(74) *Attorney, Agent, or Firm* — Timothy H. Van Dyke; Wolter Van Dyke Davis, PLLC

(57)                ABSTRACT
This disclosure provides a portable hemostatic bandage system, which comprises two formulations comprising siloxanes and blowing gas generating agents as well as a dual container device, optionally a dual syringe applicator, for in situ construction of a sponge-like polymer foam as hemostatic bandage material. Two formulations kept separately in a dual container device react instantly with each other when forced to mix, and as a result, decomposition of hydrogen peroxide occurs to generate a blowing gas $O_2$ and heat, and consequently siloxane polymer curing occurs to form polymer foam inside the dual container device. When the blowing foam is applied to a bleeding wound, it forms a sponge plug within a few minutes to control hemorrhage. This portable hemostatic bandage system can be easily used at ambient temperatures, and it is a cost-effective method to control hemorrhage.

21 Claims, 13 Drawing Sheets

(56) References Cited

U.S. PATENT DOCUMENTS

| | | |
|---|---|---|
| 9,173,817 B2 | 11/2015 | Sharma et al. |
| 2012/0107439 A1 | 5/2012 | Sharma et al. |
| 2012/0308509 A1* | 12/2012 | Mukhopadhyay .... A61L 24/001 |
| | | 424/78.37 |

OTHER PUBLICATIONS

Choudhary, Hema et al., "Foams with enhanced Rheology for stopping bleeding", ACS Appl. Mater. Interfaces 2021, 13, 13958-13967.

Ghimire, Suvash et al., "Polymeric materials for hemostatic wound healing", Pharmaceutics 2021, 13, 2127.

Sarkar, Pritha et al., "Polymer-based Coatings and Biomaterials: Research in "Hybrid Materials for Surface and Bio Applications" group", GRC, Jun. 2023.

Guo, Baolin et al., "Haemostatic materials for wound healing applications", Reviews, Nov. 2021, vol. 5, pp. 773-792.

Logun, Meghan T. et al., "Expanding Hydrophobically Modified Chitosan Foam for Internal Surgical Hemostasis: Safety Evaluation in a Murine Model", Journal of Surgical Research, Jul. 2019 (239) 269-277.

* cited by examiner

Table 1. Hemostatic functions of natural polymeric systems.

| Name [Ref.] | Polymeric System | Mechanism of Action | Case Study Model | Findings |
|---|---|---|---|---|
| Chitosan [50,91,93,95,96] | Chitosan/ε-polylysine hydrogel Chitosan-nano-bioglass composite CMCS-TA-BDBA hydrogel PVA/CSENDHM nanofibrous membrane. | Employed for hemostasis, in the form of powder, films, sponges, hydrogels, particles, fibers. Powders: Manual compression, as well as the interaction with erythrocytes, provide rapid coagulation. Hydrogels: Facilitates barrier formation and prevents blood flow from the cavity. | In vivo study of acute liver puncher models in rats, rabbits, and pigs. | Anti-microbial and anti-bacterial activities; excellent adhesion ability; rapid blood coagulation; high water absorption; biocompatible. |
| Collagen [97] | CollaStat® (Collagen and thrombin) and FloSeal® (Gelatin and thrombin) | Provides a site for platelet adherence, activation, and aggregation. The activated platelets agglomerate around the wound and stop the blood flow. | The hemostatic efficacy of CollaStat® and FloSeal® have been compared in a rabbit jejunal artery injury model. | The mean hemostasis time for CollaStat® was found to be significantly shorter compared to FloSeal® (64.0 ± 0.5 s vs. 84.0 ± 7.8 s). |

Figure 10

Table 1. Hemostatic functions of natural polymeric systems.

| Name [Ref.] | Polymeric System | Mechanism of Action | Case Study Model | Findings |
|---|---|---|---|---|
| Chitosan [50,51,91,95,96] | Chitosan/ε-polylysine hydrogel Chitosan-nano-bioglass composite CMCS-TA-BDBA hydrogel PVA/CSENDHM nanofibrous membrane. | Employed for hemostasis, in the form of powder, films, sponges, hydrogels, particles, fibers. Powders: Manual compression, as well as the interaction with erythrocytes, provide rapid coagulation. Hydrogels: Facilitates barrier formation and prevents blood flow from the cavity. | In vivo study of acute liver puncher models in rats, rabbits, and pigs. | Anti-microbial and anti-bacterial activities; excellent adhesion ability; rapid blood coagulation; high water absorption; biocompatible. |
| Collagen [97] | CollaStar® (Collagen and thrombin) and Floseal® (Gelatin and thrombin) | Provides a site for platelet adherence, activation, and aggregation. The activated platelets agglomerate around the wound and stop the blood flow. | The hemostatic efficacy of CollaStar® and FloSeal® have been compared in a rabbit jejunal artery injury model. | The mean hemostasis time for CollaStar® was found to be significantly shorter compared to Floseal® (64.0 ± 0.5 s vs. 84.0 ± 7.8 s). |

FIG. 10A

FIG. 10B
Table 1 (cont)

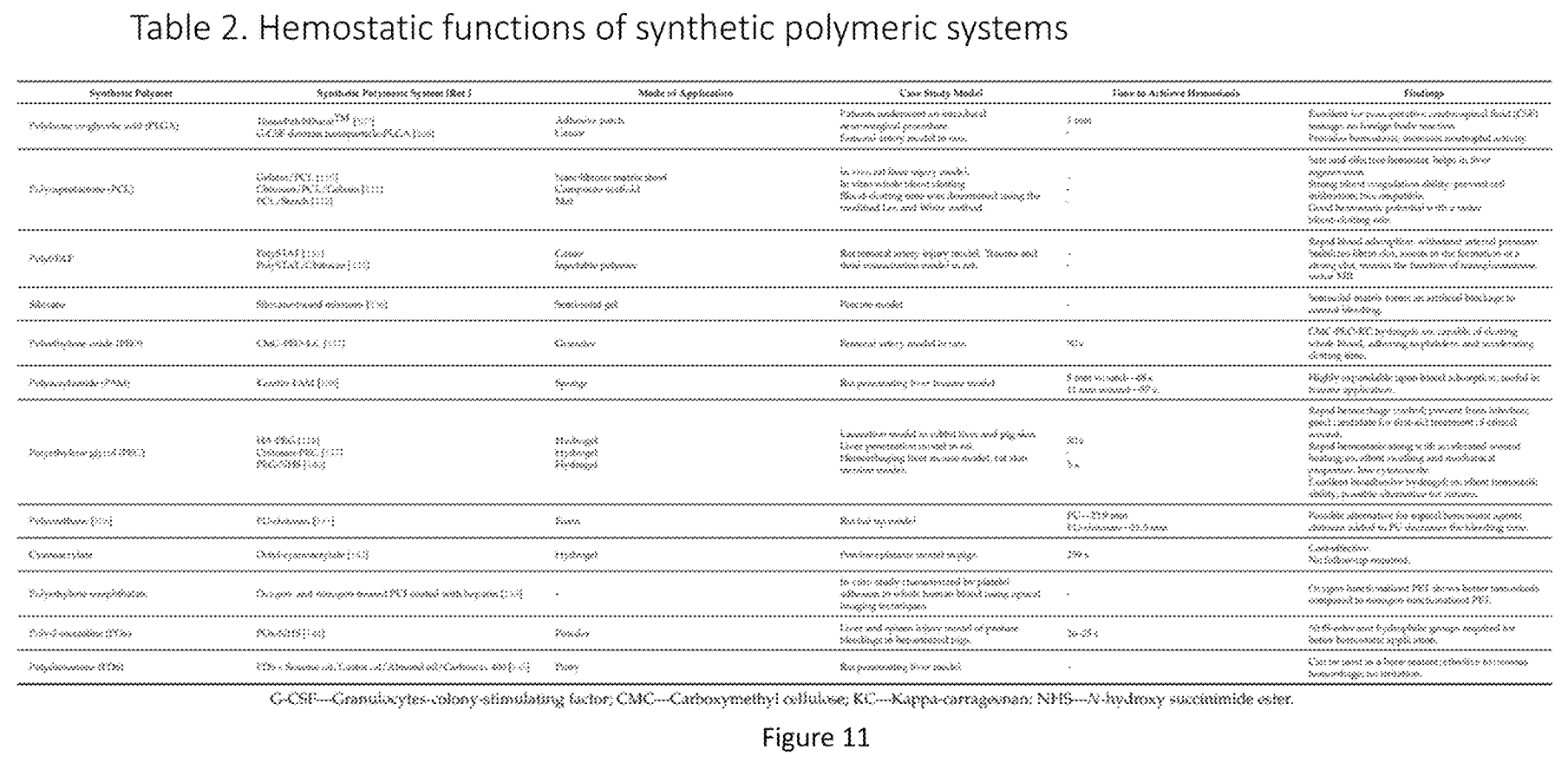

Table 2. Hemostatic functions of synthetic polymeric systems

G-CSF—Granulocyte-colony-stimulating factor; CMC—Carboxymethyl cellulose; KC—Kappa-carrageenan; NHS—N-hydroxy succinimide ester.

Figure 11

AUGMENTED THERMOSET POLYMER SPONGES FOR IN SITU HEMOSTATIC TREATMENT OF EXTERNAL AND INTERNAL WOUNDS

BACKGROUND

1. Field of the Invention

The present invention generally relates to a portable hemostatic system comprising two formulations to form polymer foam, and an application device. The invention provides a sponge-like polymer foam, in particular siloxane-based polymer foam, which is formed rapidly at ambient temperatures for in situ hemostatic treatment, as well as a delivery device for separately storing the formulations, mixing the formulations to create the polymer foam, and delivering the polymer foam to bleeding wounds external or internal.

2. Background of the Invention

Hemorrhage remains the main cause of preventable death in the battlefield. According to a statement by the US Army Medical Research and Development Command in 2022, nearly 50% of combat deaths have been due to exsanguinating hemorrhage. Most of such combat deaths have been found to occur within the first 30 minutes after wounding. Of those, about half could have been saved if timely, appropriate care had been available. In addition, in another study on combat casualties in 2012, it was found that non-compressible hemorrhage was responsible for most of the military deaths investigated. Further analysis of the data collected revealed that almost all fatalities from hemorrhage occurred before arriving at a medical facility.

While external wound injury can be treated mostly by visual inspection, internal hemorrhages are often much more intractable, causing regular hemostatic dressings to fall short because of deep wounds and obscure points of injury. The need to treat trauma wounds in the liver, stomach, colon, and spleen, accompanied by severe bleeding, and arterial, venous and/or parenchymal hemorrhage requires an immediate solution that can be applied by individual soldiers in the field swiftly and efficiently amidst military operations.

Traditional methods such as gauzes and tourniquets have gained inadequate success in terms of pressure and adhesion, and as such the fabrication of novel hemostatic materials has advanced tremendously in the last decade. However, advanced research comes at a steep cost that inflicts an economic burden of millions of dollars per year in medical care expenses, research cost, and lost productivity in the United States. Although there has been considerable success in recent years in engineering novel hemostats, developing an effective hemostatic material that is biocompatible, fast-acting, durable, with hassle-free application and removal, yet remaining a cost-effective viable option, remains a challenge.

This underscores the need to develop appropriate FDA-approved and cost-effective hemostatic treatments that can effectively stop blood loss while being easily applicable at the point-of-care, before professional medical care arrives.

SUMMARY

This disclosure provides a portable hemostatic bandage system, which comprises two formulations and a dual container device, optionally a dual syringe applicator, for in situ construction of a sponge-like polymer foam as hemostatic bandage material at bleeding wound sites. A first formulation is a mixture of a gel or solution comprising siloxane polymer and copolymer, surfactant, polymer curing catalyst, and inorganic oxide. A second formulation is a mixture of a gel or solution comprising a siloxane polymer, surfactant, and $H_2O_2$ as well as aggregate to help mixing with the former in a dual container device.

In particular, the siloxane polymer contained in both formulations is poly(dimethylsiloxane) (PDMS), and the copolymer in the first formulation is poly(dimethylsiloxane)-poly(ethylene oxide) (PDMS-PEO).

As surfactant in both formulations, a non-ionic organic detergent, Tween80™ is added.

As polymer curing catalyst, platinum-based catalyst, in particular Pt-divinyl siloxane, in more particular Pt-divinyl-poly(methylsiloxane) is used.

As foam blowing gas, $O_2$ is utilized, which is generated by decomposing $H_2O_2$ with inorganic oxide catalyst such as $Ag_2O$.

In addition, either or both of the formulations can comprise aggregate to help mixing, and silica or fumed silica is included in the second formulation in some embodiments of this disclosure.

Further, as a dual container device such as a dual syringe-type applicator having a common plunger and several turbulators dispersed in helical arrangement inside the exit tip is provided (FIGS. 1 & 2).

The main objective of the present disclosure is to provide a hemostatic bandage system that can be instantly formed at ambient temperatures, in particular a portable hemostatic bandage system, for reducing, restricting, and/or arresting, (collectively "controlling") mild, moderate, or severe hemorrhage from wounds, internal or external, in humans and other animals, so as to initiate the body's own natural blood clotting cascade. Since this is a rapidly acting—within a few minutes-hemostatic sponge plug blockage, it is especially suited for emergency situations where it is critical to control blood loss rapidly and prevent death.

One aspect of the present disclosure is to provide two formulations, which stay stable when separated from each other and react instantly with each other when mixed together. When the two formulations are mixed, two exothermic chemical reactions take place: decomposition of $H_2O_2$ to generate a blowing gas $O_2$ and heat, and consequently polymer curing of siloxanes to form polymer foam. These formulations can be packed and stored in any type of containers having two separate chambers for later use as long as the containers are suitable for field use, without any complicated instructions or with minimum training to enable error-proof administration. As an example, a dual syringe-type applicator is provided here, In certain embodiments, the portable hemostatic bandage system may include:

(a) a first formulation, which comprises:

i) about 10-100% by weight or volume of at least one siloxane polymer and copolymer;

ii) about 0-25% by weight or volume of at least one surfactant;

iii) about 0-25% by weight or volume of at least one catalyst; and iv) about 0-30% by weight or volume of at least one inorganic oxide;

(b) a second formulation, which comprises:

i) about 10-100% by weight or volume of at least one siloxane polymer;

ii) about 0-25% by weight or volume of at least one surfactant;

iii) about 1-20% by weight or volume of hydrogen peroxide; and iv) about 0-10% by weight or volume of at least one aggregate, and (c) a dual container device with a common plunger.

These unique formulations provide an easy and cost-effective approach to a portable hemostatic bandage system characterized by spontaneous self-expanding properties, which is also capable of remaining functional in inclement weather conditions, often the case in battlefields.

This product can also be used by medics, nurses, and paramedics for pre-hospital treatment of mild, moderate, or severe hemorrhage external or internal.

Conclusion: This unique strategy to develop a hemostatic dressing that contains oxygen-generating materials for supplying topical oxygen is a convenient approach for a biocompatible antibacterial hemostatic bandage system that may find utility in treating different types of skin wounds, including pressure sores, ulcers, and recalcitrant open wounds. It can also be used under inclement weather conditions, which is often the case in the fields of operation.

BRIEF DESCRIPTION OF THE DRAWINGS

The detailed description of preferred embodiments of the invention will be better understood when read in conjunction with the appended drawings. For the purpose of illustrating the invention, the drawings show certain, but not all, preferred embodiments. It should be understood that embodiments of the invention are not limited to the precise formulations and compositions of those shown in the drawings.

4

Figure 10B:
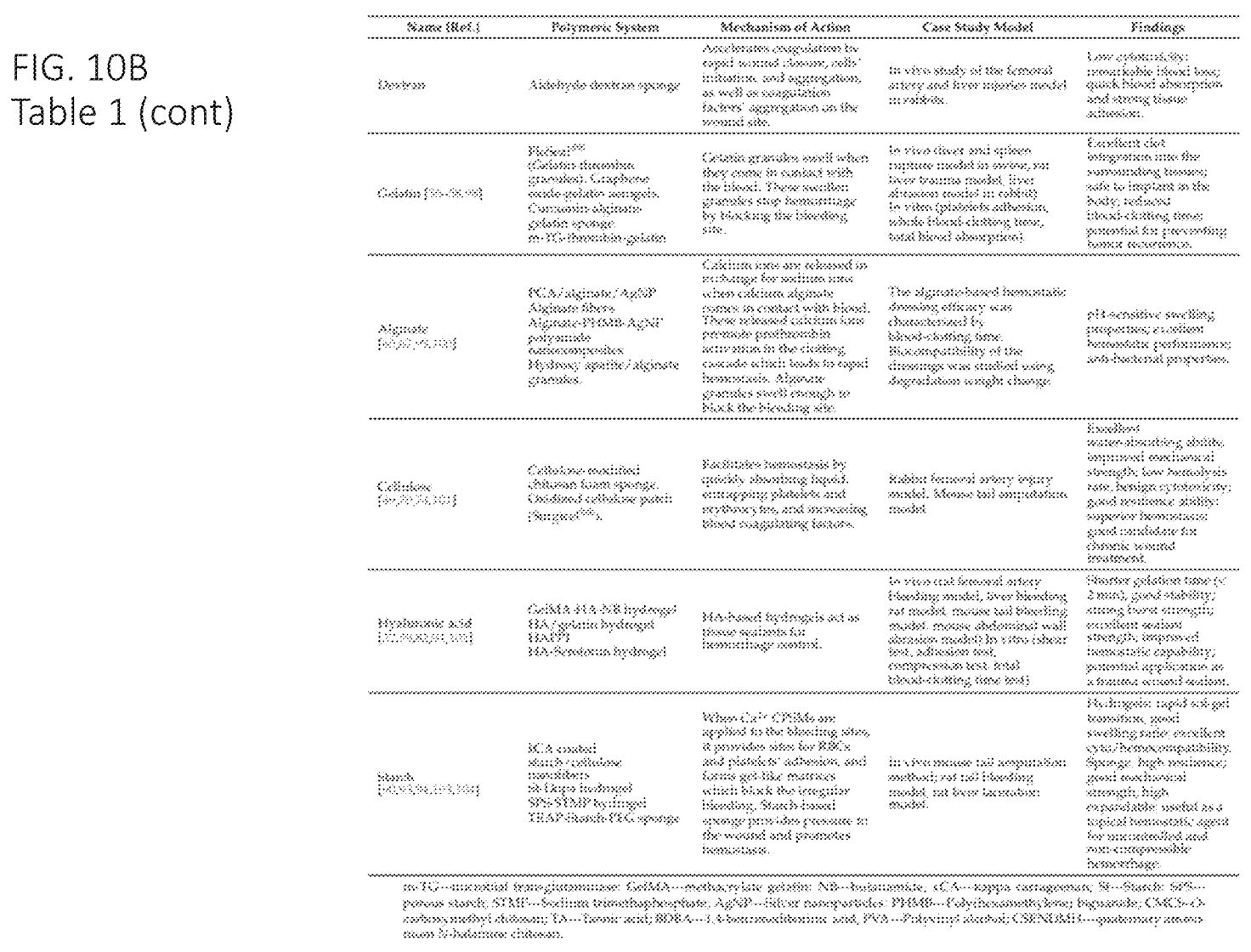
Figure 1:
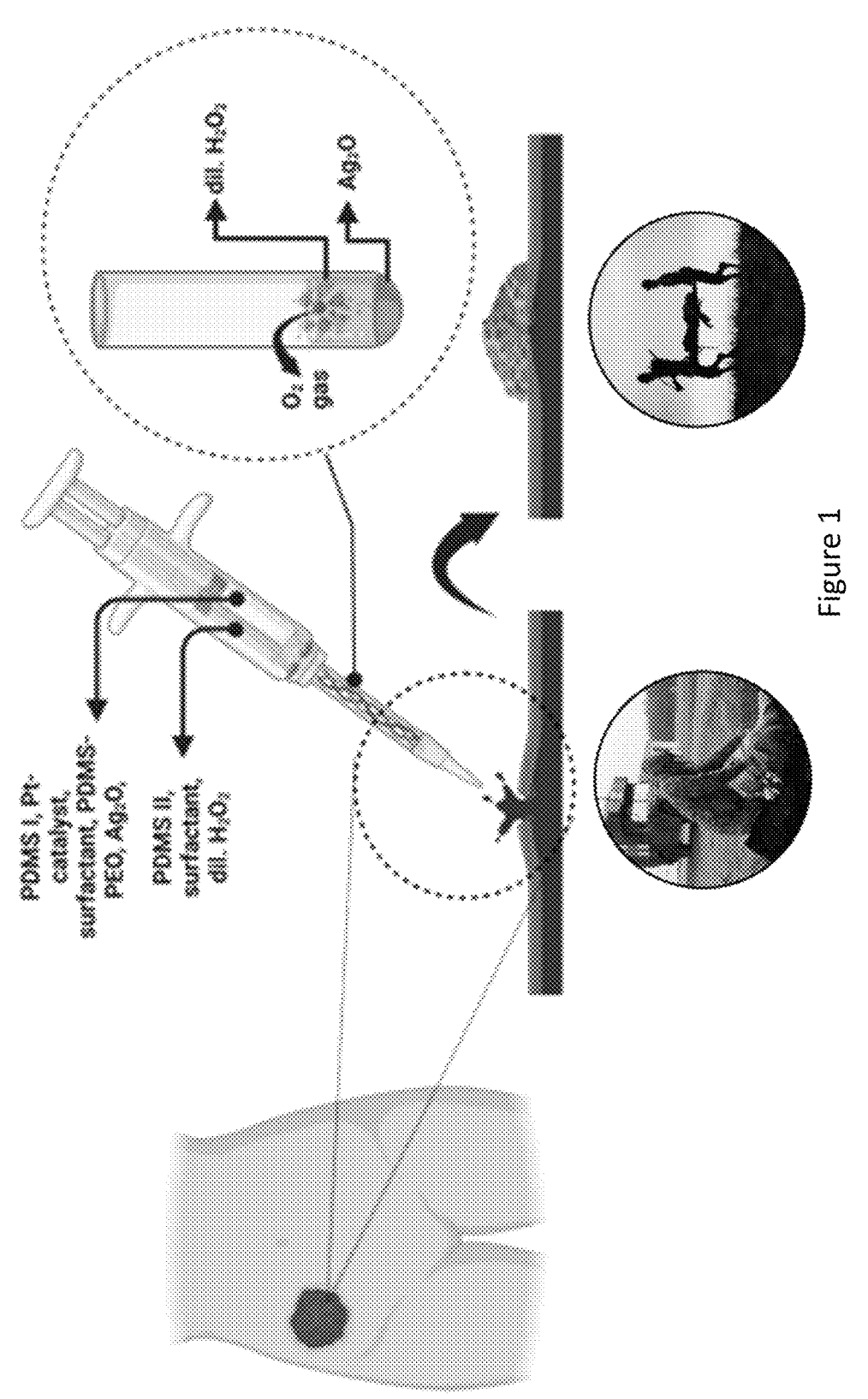
FIG. 1. A schematic representation of hemostatic sponge action. One chamber of the dual container device (e.g., a dual syringe) contains PDMS I, surfactant, Pt-catalyst, inorganic oxide (e.g., Ag$_2$O), and PDMS-PEO. The other chamber contains PDMS II, surfactant, and diluted H$_2$O$_2$. The device also has several turbulators dispersed in the exit tip space.
Figure 2:
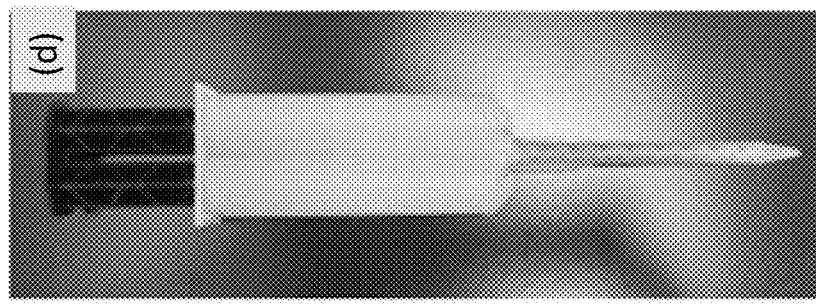
FIG. 2. Results of a foam formation test at an ambient temperature. (a) HS sponge volume expansion; (b & c) HS delivery and formation; and (d) dual syringe device for delivery.
Figure 2:
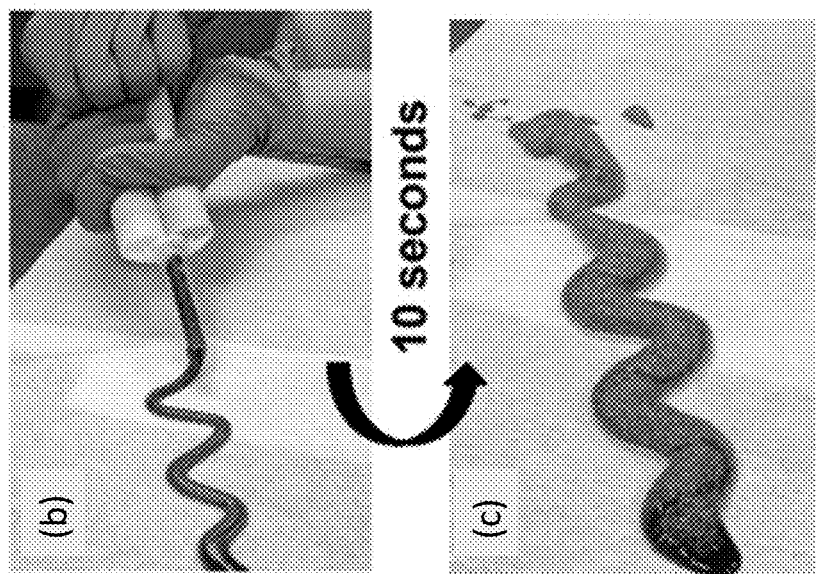
Figure 2:
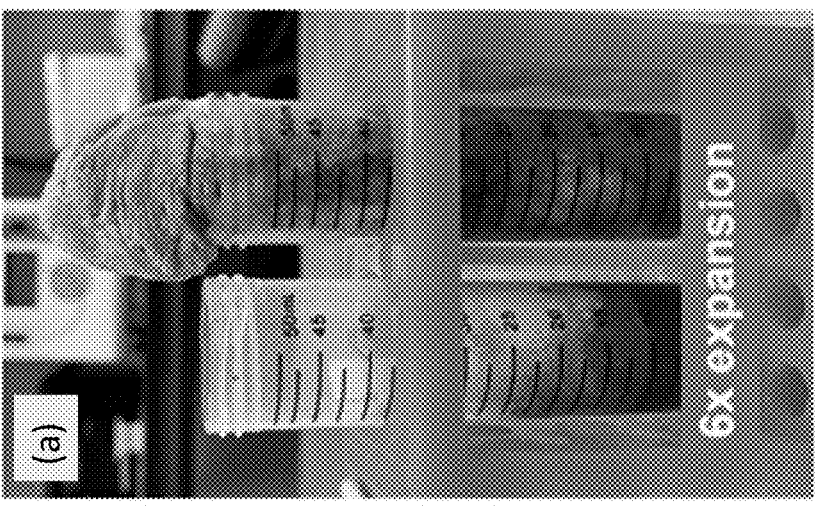

FIG. 10A and FIG. 10B shows Table 1.

FIG. 11 shows Table 2

DETAILED DESCRIPTION

A. Definitions

Unless defined otherwise, all technical and scientific terms used herein have the same meaning as commonly understood by one of ordinary skill in the art. Although various methods and materials similar or equivalent to those described herein can be used in the practice or testing of the present invention, suitable methods and materials are described below. However, the skilled artisan understands that the methods and materials used and described are examples and may not be the only ones suitable for use in the invention. Moreover, as measurements are subject to inherent variability, any temperature, weight, volume, time interval, pH, salinity, molarity or molality, range, concentration and any other measurements, quantities or numerical expressions given herein are intended to be approximate and not exact or critical figures unless expressly stated to the contrary.

As used herein, the term "about" means plus or minus 20 percent of the recited value, so that, for example, "about 0.125" means 0.125±0.025, and "about 1.0" means 1.0±0.2.

As used herein, the terms "treatment," "treating," and the like, in the context of treating a disease or condition, refer to obtaining a desired pharmacologic, medical and/or physiological effect. "Treatment," includes arresting the development or progression of the condition or disease or one or more symptoms thereof, and relieving, alleviating or ameliorating the condition or disease or one or more symptoms thereof. The term "hemostatic treatment" refers to the treatment to control, reduce, restrict, stop or arrest mild, moderate, or severe bleeding from the traumatic wound, external and/or internal in a subject.

As used herein, the term "subject" refers to any animals, and can include humans, non-human primates, other mammalians such as companion animals, farm animals, and zoo animals. A suitable subject for the invention is any mammalian suffering from moderate to severe bleeding external and/or internal.

As used herein, the term "polymer" refers to any of a class of natural or synthetic substances composed of very large molecules, called macromolecules, that are composed of multiples of unspecified number of simpler chemical units called monomers. The four basic polymer structures are linear, branched, crosslinked, and networked. Polymers are not restricted to monomers of the same chemical composition or molecular weight and structure. Some natural polymers are composed of one kind of monomer. Most natural and synthetic polymers, however, are made up of two or more different types of monomers; such polymers are known as copolymers.

Some synthetic polymer-based materials have been found useful as an artificial hemostatic material by exhibiting excellent blockage, mechanical strength, and tissue adhesion properties. Common examples of synthetic polymer-based hemostatic materials include polyesters (e.g., polycaprolactone (PCL), polylactic-co-glycolic acid (PLGA)), polycyanoacrylates, polyalkyleneoxides, polyurethane, polyethylene glycol (PEG), polyethylene oxide (PEO), polyacrylamide (PAM), polyethylene terephthalate (PET), polydioxanone (PDS), polySTAT, poly-2-oxazoline (POx), siloxane, etc. (Table 2, see FIG. 11). (Ghimire S, Sarkar P, Rigby K, Maan A, Mukherjee S, Crawford K E, Mukhopadhyay K. Polymeric Materials for Hemostatic Wound Healing. Pharmaceutics. 2021 Dec. 9; 13(12):2127; Mukhopadhyay, K.; Kasthuri, R.; Sudarshan, T. S. Siloxane-based artificial blockage to control bleeding. U.S. patent Ser. No. 00/970,7251B2, 18 Jul. 2017). These synthetic polymers can be used together with biologically derived materials such as albumin, collagen, gelatin, chitosan, keratin, polysaccharide, peptide (e.g., poly-L-lysine), alginate, dextran, starch, hyaluronic acid, oxidized cellulose (Table 1, FIG. 10) as well as other synthetic materials such as polydopamine and carbon nanotubes, to develop biohybrid matrices in the form of hydrogels, cryogels, fibrous membrane, or granules for wound dressings.

The term "rheological additive" means an ingredient or combination of ingredients that increase the viscosity of, or thicken, the composition, and if particulates are present, may also suspend the particulates in the composition. Suitable associative thickeners generally contain a hydrophilic backbone and hydrophobic side groups. Examples of such thickeners include polyacrylates with hydrophobic side groups, cellulose ethers with hydrophobic side groups, polyurethane thickeners. Examples of hydrophobic side groups are long chain alkyl groups such as dodecyl, hexadecyl, or octadecyl; alkylaryl groups such as octylphenyl or nonyphenyl. Rheological additives may also include natural or synthetic montmorillonite minerals.

As used herein, the term "siloxanes" refers to molecules with an oxygen-silicon backbone (Si—O—Si:

$$\overset{\displaystyle\diagdown}{\underset{\displaystyle\diagup}{\text{Si}}}\diagdown_{\text{O}}\diagup\overset{\displaystyle\diagup}{\underset{\displaystyle\diagdown}{\text{Si}}}\ ),$$

where each Si atom carries two organic groups, mostly methyl, ethyl or phenyl groups. Siloxanes are commonly known as silicones. They belong to the organosilicon compounds and are exclusively obtained by synthesis. Importantly, they are non-toxic and will not cause harm to biological systems, including humans and animals. Non-limiting examples include polydimethyl siloxane (PDMS), polydimethylsiloxane-poly(ethylene oxide) (PDMS-PEO) copolymer, divinylpolymethylsiloxane. divinyltetramethyl-disiloxane, methylhydrosiloxane, dimethylsiloxane, methyl-hydrosiloxane-dimethylsiloxane copolymer, and combinations thereof.

Figure 7:
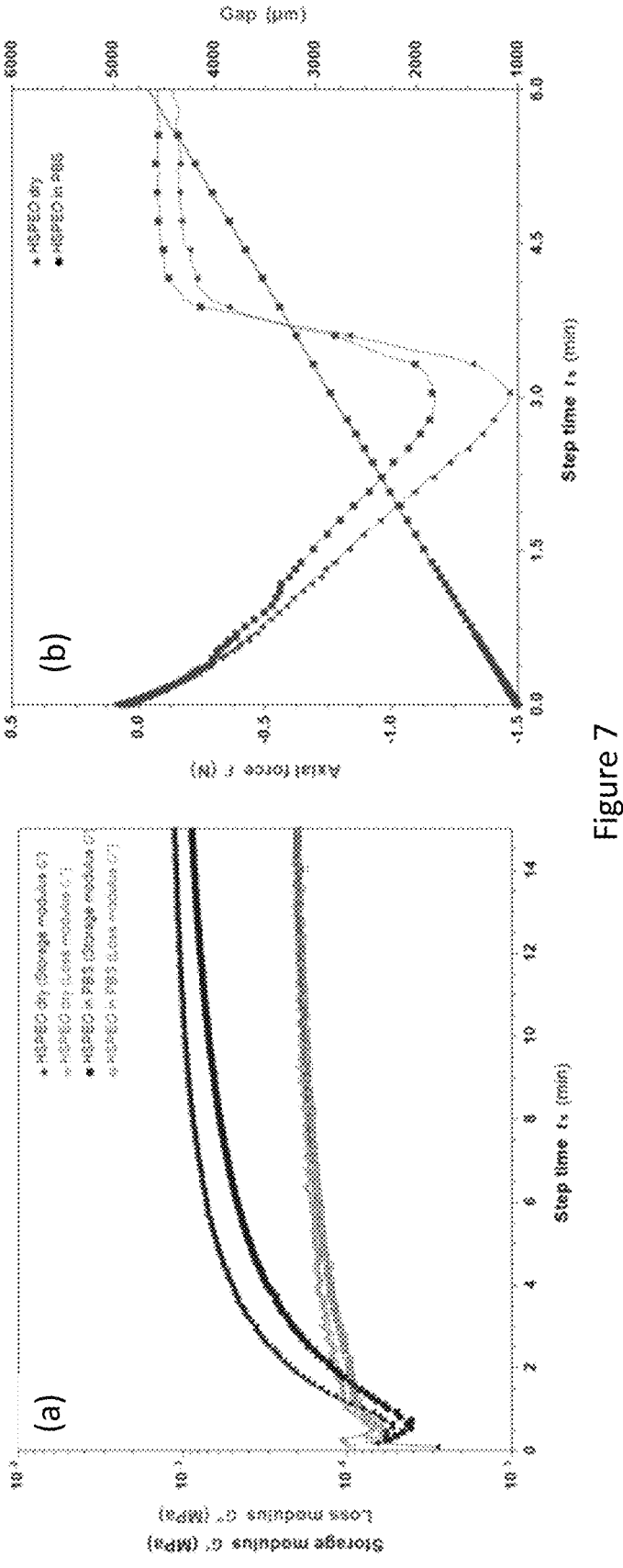
FIG. 7. (a) Rheological performance of hemostatic sponge in both dry and wet (PBS) environments represented by oscillatory time sweep of liquid-to-foam reaction; (b) axial test demonstrating adhesion performance.

As used herein, the term "polymer curing" refers to a chemical process that produces the toughening or hardening of a polymer material by cross-linking of polymer chains. During the curing process, single monomers and oligomers, mixed with or without a curing agent, react to form a tridimensional polymeric network. Curing can be induced by heat, radiation, electron beams, or chemical additives. During a curing process, the system has lost its solubility, and its viscosity tends to increase. The degree of crosslinking determines the rigidity and durability, as well as other properties of the material. In many cases, the polymer resin is provided as a solution or mixture with a thermally-activated catalyst, which induces crosslinking but only upon heating. The material, initially liquid, will be solid at the end of the process: viscosity is the most important property that changes during the process. A simple way to monitor the change in viscosity, and thus, the extent of the reaction, in a curing process is to measure the variation of the elastic modulus using a rheometer. With dynamic mechanical analysis, the storage modulus (G') and the loss modulus (G")

can be measured. The variation of G' and G" in time can indicate the extent of the curing reaction. As shown in FIG. 7, after an "induction time", G' and G" start to increase, with an abrupt change in slope. At a certain point they cross each other; afterwards, the rates of G' and G" decrease, and the moduli tend to a plateau. When they reach the plateau, the reaction is concluded. When the system is liquid, the storage modulus is very low: the system behaves like a liquid. Then the reaction continues, and the system starts to react more like a solid: the storage modulus increases. The degree of curing, a, can be defined as follows:

$$\alpha = \left(G'_{(t)} - G'_{min}\right)/\left(G'_{max} - G'_{min}\right)$$

The degree of curing starts from zero (at the beginning of the reaction) and grows until one (the end of the reaction). The slope of the curve changes with time and has its maximum about at half of the reaction.

In one embodiment, the curing process (polymer cross-linking) of siloxane polymers is initiated by the heat generated when $H_2O_2$ is decomposed to $O_2$ and $H_2O$, an exothermic reaction. Since polymer crosslinking is another exothermic reaction, the heat generated by both chemical reactions promote further polymer crosslinking until either or both of the reaction substrates (long linear polymers such as poly(dimethylsiloxane)(PDMS) and polydimethylsiloxane (PDMS)/poly(ethylene oxide) (PEO), and/or single monomers/oligomers are completely crosslinked. Since this system utilizes heat generated by $H_2O_2$ decomposition as activation energy to overcome the reaction threshold of polymer crosslinking at the initiation step, this principle of pairing polymer curing with another exothermic reaction within the same reaction mixture may be applied to other polymer curing processes.

B. Overview

The purpose of this disclosure herein is to provide patients, especially those in battle fields of action, with a means to rapidly control bleeding from external and internal wounds in a simple and effective manner superior to those currently available.

To this end, a novel, rapidly self-expanding, polymer-based bandage system is provided, which forms sponge-like polymer foam at ambient temperatures of 5° C. to 25° C. within a few minutes (about 2 minutes). The invention also contains oxygen-generating materials for generating blowing gas and heat as well as supplying topical oxygen, which is a convenient approach for a biocompatible antibacterial hemostatic bandage system that may find utility in treating different types of skin wounds, including pressure sores, ulcers, and recalcitrant open wounds. In addition, the invention disclosed herein is easy to use and cost-effective, and can remain functional in inclement weather conditions, which is often the case in battlefields and fields of operation.

C. Two formulations (Part A and Part B)

The hemostatic polymer foam is made from two formulations containing polymer mixture gels each, and a dual container device for keeping the two formulations separately, mixing the two formulations, and applying the resultant sponge-like polymer foam to a mild, moderate, or severe hemorrhage site, external and/or internal.

7

(a) Polymer

A first formulation gel/solution (designated for reference purposes only as "Part A") comprises a mixture comprising at least one type of polymer, at least one surfactant, calculated volume of blowing agent A, and at least one polymer curing catalyst. Similarly, a second formulation gel/solution (designated for reference purposes only as "Part B") comprises a mixture comprising at least one type of polymer, at least one surfactant, calculated volume of blowing agent B, and at least one aggregate. The two formulations are kept separate until use. The blowing agent A and the blowing agent B are stable when they are kept separate, and they react instantly with each other to generate a blowing gas when mixed together in a dual container device.

The polymer(s) in the formulations can be a single type- or a mixture of more than one type of biocompatible polymer(s). The polymer(s) in Part A and Part B can be at least one selected from siloxanes, functional siloxanes, polyurethanes, polyacrylates, polymethylmethacrylates, epoxies, vinyl-terminated polymers, copolymers. The polymer(s) in Part A and Part B can be the same type of a polymer or mixture of polymers, or the polymer(s) in Part A can be different from that/those in Part B.

(b) Surfactants

The surfactant included in the formulations acts to reduce agglomeration and resultant potential sedimentation of the components, and consequently enhances the ability of the components in the solutions or gels to mix readily. The surfactant may be anionic, cationic, amphoteric, Gemini, non-ionic, or a combination of all types.

When the sponge-like polymer foam is used for hemostatic treatment, the use of a non-toxic surfactant is necessary The non-limiting examples of such non-toxic biosafe surfactants include, but not limited to polyoxyethylene sorbitan monolaurate (Tween™ 20), polyoxyethylene sorbitan monopalmitate (Tween 40™), polyoxythylene sorbitan monostearate (Tween 60™) polyoxyethylene sorbitan monooleate (Tween 80™), and polyoxyethylene (10) iso-octylcyclohexyl ether (Triton X-100™), polyethylene glycol tert-octylphenyl ether (Triton X-114™), other poly(ethylene oxide)-based surfactants, polyoxyethylenated alkylphenols, polyoxyethylenated alcohols, monoglycerides of long-chain fatty acids, and the like. The surfactant(s) in Part A and Part B can be the same kind, or the surfactant(s) in Part A can be different from that/those in Part B.

(c) Polymer Curing Catalyst

One formulation comprises a curing catalyst for polymer curing. Examples of catalysts include, but are not limited to platinum (Pt), tin (Sn), titanium (Ti), zirconium (Zr), calcium (Ca), zinc (Zn)-compounds, complexes, and salts. Other noble metals, including palladium, rhodium and the like and their respective compounds, complexes, and salts can also be contemplated as catalysts. However, the system can also be implemented with heat-curing or UV-curing resins.

(d) Aggregate

In addition, an aggregate can be included in either or both of the formulation to help a micro-kinetic mixing mechanism. Optionally, the aggregate is a small, non-reactive compound. A non-limiting but good examples of such an aggregate are silica, fumed silica, basalt, felspar, clay, zeolite, aluminosilicates, mesoporous materials. When the formulations are mixed, the aggregate particles act as local micro-stirrers that push, pull, carry, and mix the components thanks to their abrasive properties.

8

(e) Rheologic Additives or Particle Fillers

Either Part A or Part B may comprise rheologic additives or particle fillers. The content of the rheological additive(s)/particle filler(s) is about 0%-10% by weight or volume of the formulation.

(f) Blowing Gas

Part A and Part B comprise a blowing agent A and a blowing agent B, respectively. Blowing agent A and blowing agent B, when being kept separately, are stable, but when mixed together, react with each other to generate a blowing gas. Examples of the blowing gas to be used include but are not limited to carbon dioxide, oxygen, ozone, nitrogen, nitrous oxide, nitric oxide, phosphine, or combination of thereof, and any blowing agents to generate these blowing gases can be contemplated, in particular blowing gases generated by exothermic reactions When the components described above are all mixed to form the formulation Part A and the formulation Part B, they are sterilized before being packed into a dual container device.

D. Dual Container Device

When sponge-like polymer foam is used for a hemostatic purpose, it is preferable that the polymer foam is formed instantly right before use. Therefore, a dual container device can be contemplated for mixing the formulations at the same space, where mixing of two formulations is enhanced by the inclusion of aggregates such as fumed silica ($SiO_2$) as local micro-stirrers, and for applying the resultant foam to a bleeding wound easily and quickly, especially when a hemostatic bandage system is intended for emergency use in the battlefield.

The dual container device is a hand-powered device made of synthetic resin or plastic, solid or elastic, for optionally a single use, and it is sterilized by gamma irradiation. The dual container device has three functions, i.e., for keeping the formulations separately from each other before use, mixing the two formulations together to initiate the chemical reactions, and applying the resultant polymer foam to the bleeding wound.

For these functions, the device has two separate chambers, a common exit tip space where mixing of Part A and Part B takes place, a syringe needle-like narrow open cylinder (i.e., common exit tip), and a common force applier at the opposite side to the common exit tip, and it can be any container device having those parts. The two chambers of the device can contain a premeasured volume, optionally 1 to 1000 mL, of the two sterilized formulations, respectively. Those chambers open to the common exit tip space through a small hole (about 0.1 to about 10 mm) and the common exit tip space (funnel shaped or pouch shaped?) is connected to the syringe needle-like cylinder (length and diameter?) which has an opens end at the opposite side to the chamber opening holes, in order to extrude the polymer foam from the device.

For example, the dual container device can be a dual syringe having a wall between the two chambers and a common plunger that can push out the two formulations simultaneously at the same force and velocity, or it can be two tubes fixed together, having a common rolling- or pushing tube squeezer equipped at one end of those tubes at the same side, which can be rolled or pushed to squeeze out the two formulations simultaneously.

To administer the sponge-like polymer foam to the bleeding site, a user directs or inserts the syringe needle-like cylinder (i.e., common exit tip) into the edge of the wound, and pushes or squeezes out the formulations to the bleeding site, moving the device in a circular motion to the center of the wound.

In addition, this dual container device has a plurality of turbulators disposed inside the common exit tip space in a helical arrangement so that the mixtures passing through the tip are stirred and agitated to aid in mixing process. (e.g., turbulator-dispersed dual-syringe device). Although many shapes and configurations of the turbulators are contemplated, one preferred embodiment for adequate mixing performance inside the tip includes about 5 to 10 turbulators in a helical arrangement at the center of the tip space. The turbulators are rudder-like, and most optionally are segments of planar helix with the segments offset 180 degrees about the axis of helix-wrap from one another.

The two parts are mixed together at rates that can vary from 0.1 mm/s to 100 mm/s. When Part A and Part B formulations are properly mixed, the formulations react with each other in situ to form a polymeric matrix, which comes out of the tip in the shape of a nearly cured soft-solid, self-expanding flexible sponge-like polymer foam that can temporarily adhere to the surface of a bleeding wound of any shape, size and depth, thereby acting as an artificial plug by creating an autogenous pressure on the bleeding wound site with bleeding rates varying from 0.01 mL/s to 100 mL/s. This physical sponge plug stops mild, moderate or severe bleeding, initiating the body's natural clotting cascade. An occlusive bandage can be placed on top of the expanding polymeric matrix, to contain it within the wound space. Once the patient has received medical attention, the hemostatic plug can be removed.

The adhesion of the sponge to surfaces has been studied and it has been adjudged that they may be easily and painlessly removed after triage. The composition sticks to the bleeding site and partially adapts to it, making it useful as a hemostatic treatment. This can happen in or on a wound. The actual compounds utilized, together with the weight and volume of the component parts of the compositions, may differ from one another and still result in a certain type of blockage, but specific ranges result in compositions with the most desired properties.

The polymer foam can be augmented to exhibit hydrophilic, hydrophobic, oleophilic, oleophobic, lipophilic, lipophobic, omniphilic, omniphobic properties, and particulate and dust repellency, and have different surface energies and surface properties based on foam formation and their pore structures. Depending on the formulations, the polymeric foams and sponges may also exhibit antibacterial properties including antibacterial, antifungal or antipathogenic efficacy.

E. Exemplary Embodiments (a) $O_2$ as Blowing Gas

In certain embodiments, the hemostatic bandage system uses $O_2$ as a blowing gas. The heat generated during the decomposition of $H_2O_2$ to $O_2$ and $H_2O$ serves two purposes. It acts to initiate and speed up the cross-linking between the polymers to form the resultant sponge-like polymer foam, and to facilitate the mixing of the formulations of Part A and Part B by decreasing the viscosity of the components.

In preferred embodiments, Part A comprises a mixture comprising siloxanes as polymer(s); platinum-based curing catalyst (e.g., Pt-divinyl siloxane catalyst such as platinum divinyl-polymethylsiloxane) or zinc-based or tin-based catalysts; calculated volume of $Ag_2O$ as an inorganic oxide (as blowing agent A, i.e., a catalyst for decomposition of hydrogen peroxide), and a non-ionic organic surfactant (e.g., polyoxoethylene sorbitan monooleate (i.e., Tween 80™)) Tween 80™ is non-toxic, and has been used in other medical, food, and cosmetic products.

In a preferred embodiment, siloxane in Part A is poly (dimethylsiloxane) (PDMS), and poly(dimethylsiloxane)-poly(ethylene oxide) (PDMS-PEO) copolymer can be added to enhance the hydrophilicity of the sponge surface. In another embodiment, Part A comprises PDMS and methyl-hydrosiloxane-dimethylsiloxane (a copolymer). Optionally, the ratio between PDMS and copolymer can be 1:0.1 to 1:10. In Part A, the content of whole siloxane polymers is about 10-100%, in particular about 75-90%, and in more particular about 84%, by weight or volume. Part A also comprises about 0%-25% surfactant, about 1%-30% inorganic oxide, and about 0%-25% catalyst, by weight or volume.

As blowing agent A, in addition to $Ag_2O$, a variety of inorganic oxides can be contemplated over a range of concentrations in order to determine the best composition and optimize both expansion and temperature. Iron oxide (e.g., $Fe_2O_3$, $Fe_3O_4$, or $FeO$) or any iron salt (e.g., iron chloride, iron nitrate, iron sulfate, and ammonium iron sulfate), and Group II alkaline-earth metal salt/oxide, including magnesium (MgO) and calcium (CaO), can also be contemplated. Group II metal salts/oxides can also help releasing a polymer curing catalyst if the curing catalyst is bound to a siloxane. For example, in an embodiment comprising platinum divinyl-polymethylsiloxane, the platinum, i.e., the polymer curing catalyst, is dissociated by the aid of Group II salts/oxides. These Group II metal oxides can be replaced with any $H_2O_2$-decomposing compound. Such compounds include tin (Sn), manganese (Mn), nickel (Ni), cobalt (Co), titanium (Ti), and chromium (Cr), as well as hydroxide (OH—) and sulfate.

Similarly, Part B comprises a mixture comprising PDMS as polymer(s), surfactant (e.g., Tween80™), calculated volume of diluted $H_2O_2$ in water (as blowing agent B), and fumed silica such as vinyl modified Q silica resin (<30%) as aggregate. The silica or fumed silica aggregate can also be included in Part A, if need be.

In Part B, the content of siloxane polymer is about 10-100%, in particular 75-85%, and in more particular about 82%, by weight or volume. The concentration of hydrogen peroxide is about 5-18%, and optionally about 17.5%, by weight or volume of Part B. Part B also comprises, by weight or volume, about 0-25% surfactant and about 4-4.5% aggregate(s).

When Part A and Part B react with each other, decomposition of $H_2O_2$ to form $O_2$, $H_2O$ and heat ($H_2O_2$ ((or urea hydrogen peroxide)→$O_2$+$H_2O$+heat) occurs, which is an exothermic reaction. That is, when a solution containing hydrogen peroxide or urea hydrogen peroxide contacts with a solution containing alkaline salt/oxide and/or iron salt/oxide, the inorganic salt/oxide serves as a catalyst for decomposing hydrogen peroxide as described above. Hydrogen peroxide is completely or nearly completely decomposed upon mixing the two solutions, which reduces or avoids the possibility of irritation or stinging caused by $H_2O_2$ in or on the wound site of the human or animal subject. The oxygen foams up the siloxane polymers to form the sponge-like foam. The generated heat initiates polymer crosslinking, another exothermic reaction, by providing energy to overcome the threshold of the initial polymer crosslinking reactions, which results in more heat and more polymer crosslinking.

In addition, particle fillers can be optionally included in either of the formulations. Non-limiting examples of particle fillers include oxides, hydroxides, peroxides, suboxides, superoxides, mixed oxides, carbonates, hydrogen carbonates, phosphates, hydrogen phosphates, sulfates, hydrogen sulfates, nitrates, fluorides, chlorides, bromides, iodides, cyanates, isocyanates of magnesium, calcium, barium and strontium.

(b) $CO_2$ as Blowing Gas

In another embodiment, the hemostatic bandage system can use $CO_2$ as a blowing gas. In this system, Part A comprises a mixture of polymer, a curing catalyst, calculated volume of inorganic bicarbonate, inorganic carbonate and/or inorganic carbamate, and a surfactant. Similarly, Part B comprises a mixture of polymer B, calculated volume of organic and/or inorganic acids or organic anhydride (e.g. acetic anhydride), or acid salts, aggregates, and a surfactant. Here, the bicarbonate can be at least one selected from the group consisting of bicarbonates of sodium, potassium, aluminum and iron, and the acid can be at least one selected from the group consisting of maleic acid, citric acid, acetic acid, succinic acid, tranexamic acid, mandelic acid, tartaric acid, or mixture of these acids in certain proportions thereof.

When Part A and Part B react with each other, the following reaction takes place with a pre-calculated stoichiometry based on an empirical formula: $AHCO_a + C_bH_cO_d \rightarrow A^+ + C_eH_fO_g^{a-} + H_2O + CO_2$; the liberation of carbon dioxide foams up the polymer matrix to form a sponge-like foam in less than a minute.

A variety of acids, carbonates and bicarbonates, mixture of carbonated and bicarbonates with stoichiometric amounts can be contemplated to augment such reactivity with polymeric systems over a range of concentrations in order to determine the best composition so as to optimize both the expansion of the sponge-like foams, as well as controlling the reaction temperature to avert possible risks of embolism and burns from heat of reaction.

An exemplary description of one such system is:

Part A includes:

i) about 0.1-100% by weight or volume of at least one polymer;

ii) about 0.01-50% by weight or volume of at least one surfactant;

iii) about 0.001-50% by weight or volume of at least one catalyst;

iv) about 0.1-50% by weight or volume of blowing agent A;

v) optionally, an amount of an inorganic, the inorganic may include but is not limited to oxides, hydroxides, peroxides, suboxides, superoxide, sulfides, sulfates, persulfates, phosphides, carbonates, bicarbonates, nitrides, azides, thiosulfates, thiols, nitrates, silicates, aluminosilicates, clays, zeolites, felspar, basalt;

vi) optionally, provision of incorporation of painkillers/antibiotics/antibodies, or any other agent with properties conducive to patient health;

vii) a viscosity ranging from 1 cP to 1000000 cP; and

Part B includes:

i) about 0.01-100% by weight or volume of at least one polymer;

ii) about 0.001-50% by weight or volume of at least one surfactant;

iii) about 0.01-50% by weight or volume of blowing agent B;

iv) about 0.001-50% by weight or volume of at least one particle filler or rheological additive;

v) optionally, an amount of an inorganic, the inorganic may include but is not limited to oxides, hydroxides, peroxides, suboxides, superoxide, sulfides, sulfates, persulfates, phosphides, carbonates, bicarbonates, nitrides, azides, thiosulfates, thiols, nitrates, silicates, aluminosilicates, clays, zeolites, felspar, basalt;

vi) a viscosity ranging from 0.1 cP to 1000000 cP;

In certain embodiments, a dual container device for formulation storage and mixing, and sponge-like polymer foam application is a dual-syringe applicator having a common plunger and turbulators dispersed inside, in which the sterilized formulations of Part A and Part B can be contained and sealed.

F. Advantages of this Invention

The siloxane polymer disclosed here involves conversion process from a gel/solution to foam type within ambient temperatures of 5° C. to 25° C., which is starkly different from any other types of foam-based hemostatic bandage system. Most of them involve temperatures greater than 35-40° C. Coupling exothermic reaction of $O_2$ generation from $H_2O_2$ to polymer curing process in this disclosure is a significant advantage and benefit over previous hemostatic systems that involves self-curing process.

Overall, the sponge-like polymer foam made from two formulations comprising siloxane polymers of this disclosure has several advantages; (1) light-weight, inexpensive, and easily applicable, (2) biocompatible and non-toxic (as demonstrated in Examples), FDA-compliant, (3) hydrophobic and usable in all weather conditions, (4) easily removed without embolism, or any form of tissue, muscular, or vascular damage, and (5) ability to conform, contour in and around the wound to form an artificial blockage and to stop bleeding associated with internal wounds (abdominal, liver, colon) using autogenous-pressure approach. In addition, with various viscosities and shore hardnesses of siloxanes, these sponges will exhibit superior rheological/mechanical properties compared with many existing foam bandage systems disclosed in prior art.

Furthermore, this disclosure provides a portable device that enables adequate mixing of two formulations in gel or solution to create a sponge-like polymer foam applicable to bleeding wounds, without requiring any professional hands or complicated procedures or measurements to ensure accuracy. This hand-held device can be easily stored, carried, and easily implemented by medics, nurses, self, and combatants with simple instruction and minimum training.

Besides, the cost of such an applicator (product/package) as a dual syringe suggested here is estimated around $150, which is much cheaper compared to 3-patch TachoSil package that is a fibrin-based sealant and costs $2200 in the market.

Considering all these aspects, the portable hemostatic bandage system disclosed here can be used to create an instant sponge plug in situ, which will trigger the body's own clotting cascade. This type of polymer foam can find other use, functioning as cushioning and flexible substrates and shape memory foams. The system can be used to control hemorrhage from wounds, internal or external, in people and other animals, and it is particularly suited for emergency situations when it is essential to limit blood loss in times of panic or crisis. In addition, bioactive agents such as painkillers, antibacterial and/or antifungal agents, antibodies, and/or any other bioactive agents can be introduced into the structure of the sponge-like polymer foam to further complement hemostatic and regenerative action.

Support data will include detailed characterization of the polymers and the hemostatic sponge formed upon reaction. Studies on mechanical durability, surface adhesion, hydrophobicity, SEM image analysis, spatiotemporal analysis, along with additional in-vitro assays will also be presented.

EXAMPLES

Example 1. Materials and Methods

The hemostatic bandage system comprises two formulations (Part A and Part B) and a device for storing and mixing the two formulations and applying the resultant sponge-like siloxane polymer foam, which contains $O_2$ as a blowing gas, to a bleeding wound to control mild, moderate, and severe hemorrhage.

Part A comprises a mixture comprising siloxane polymer, PDMS, and co-polymer PDMS-PEO, a Pt-based curing catalyst, calculated volume of inorganic oxide (e.g. $Ag_2O$, a surfactant. The Pt-based curing catalyst is a Pt-based siloxane, e.g., platinum divinyl-polymethylsiloxane. The surfactant is a non-ionic organic surfactant such as poly-oxyethylene sorbitan monooleate (Tween 80™). PDMS-PEO copolymer enhances the hydrophilicity of the sponge surface.

Similarly, Part B comprises a mixture comprising siloxane polymer, PDMS, calculated volume of 50% $H_2O_2$ in water, silica, and surfactant. The surfactant is polyoxyethylene sorbitan monooleate (Tween 80™). As aggregate, silica or fumed silica may be added to the formulation Part B.

To administer, the formulations are simply mixed using a dual-syringe applicator having a plurality of turbulators inside. When Part A interacts with Part B inside the device, two types of reactions take place: decomposition of $H_2O_2$ to form $O_2$ gas and $H_2O$ ($H_2O_2 \rightarrow O_2 + H_2O + heat$) catalyzed by inorganic oxide $Ag_2O$, and polymer curing of siloxanes catalyzed by the Pt curing catalyst. The generation of oxygen gas foams up the poly-siloxane matrix so as to form the sponge-like foam in situ in less than a few minutes. The sponge-like foam is self-expanding and flexible, and conforms on and around the wound, thereby acting as an artificial sponge plug creating an autogenous pressure on the site of injury to arrest bleeding.

All polymers were obtained from Gelest Inc. Remaining chemicals were obtained from Fisher Scientific.

Example 2. Formation of Spongy-Like Foam

Several inorganic oxides (Ag2O, hydrogen peroxide, and the like) or organic oxides (e.g. urea hydrogen peroxide), were tested over a range of concentrations in order to develop foams having optimal mechanical properties to control bleeding. The selection of these oxides was also based on their inherent biological benefits in promoting the coagulation cascade and imparting antimicrobial properties. Of the tested inorganic oxides, $Ag_2O$ was seen to produce the best results.

Figure 3:
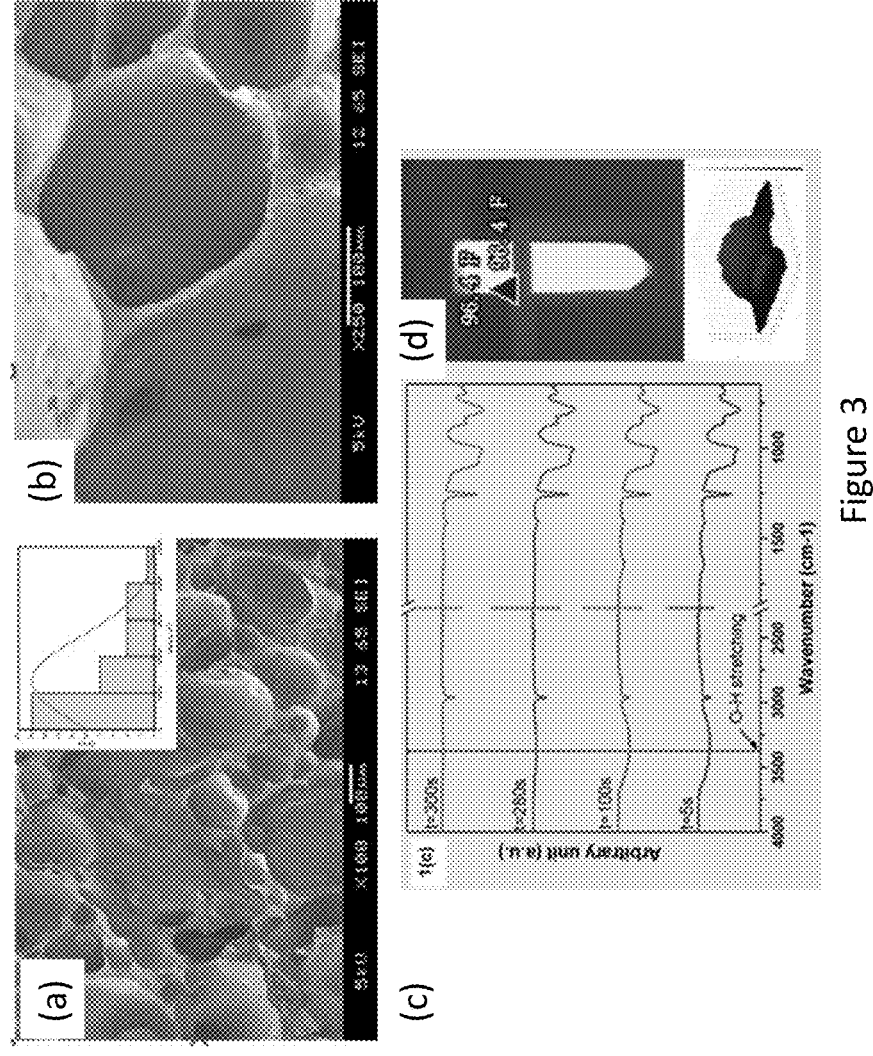
FIG. 3. (a & b) SEM images of hemostatic sponge morphology; (c) in situ ATR-FITR of foaming reaction; and (d) thermal imaging of sponge on expansion showing temperature optimization of the heat of reaction.

The resultant foam was then characterized for SEM image analysis (FIG. 3).

The following support data include detailed characterization of the synthesized polymers and the hemostatic sponge formed upon reaction. Studies on mechanical durability, surface adhesion, hydrophilicity/hydrophobicity, spatiotemporal analysis, along with additional in-vitro assays are also presented.

Figure 4:
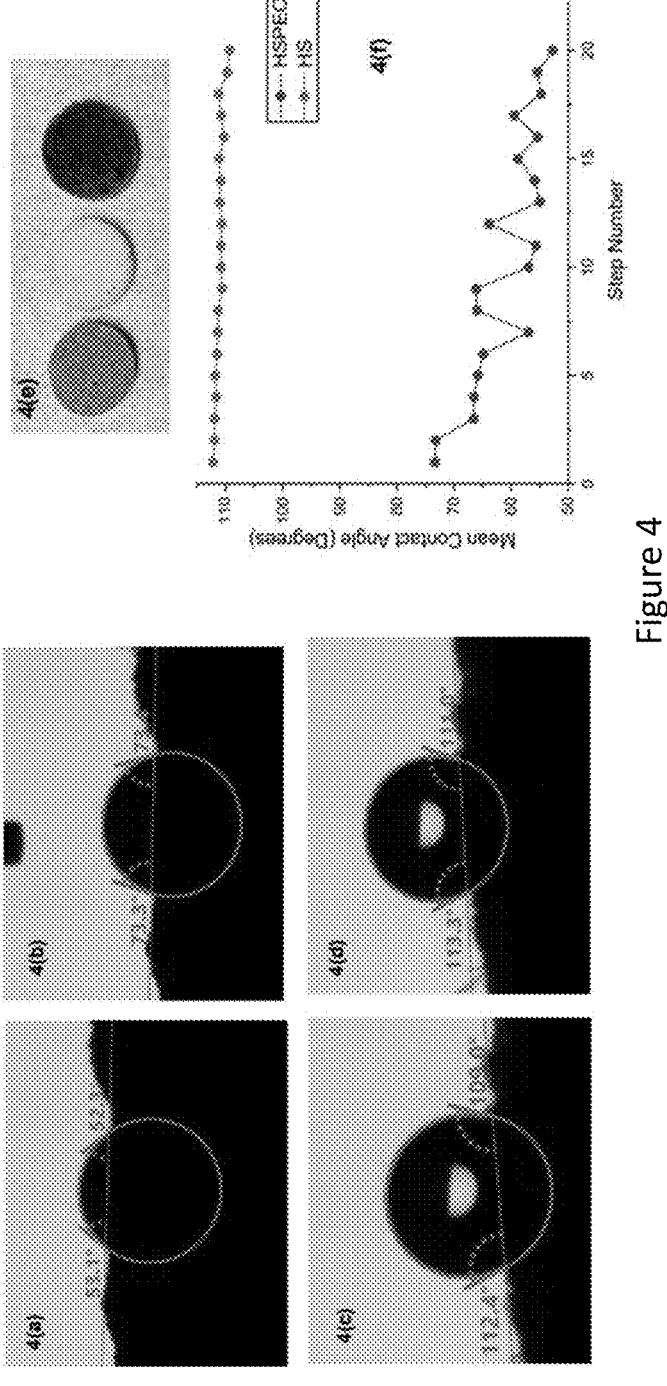
FIG. 4. Contact angles indicating sponge hydrophilicity for (a & b) HS-PEO sponge and for (c & d) HS sponge; (e) cross sections of hemostatic sponges; and (f) contact angle variation with time.

Example 3. Characteristics of the Spongy-Like Foam (1) Hydrophilicity/Hydrophobicity of the Surface The hydrophilicity/hydrophobicity of the surface of the sponges have been determined by contact angle goniometry (FIG. 4). FIGS. 4a & 4b show that HS-PEO sponge has lower contact angle and better hydrophilicity compared with HS sponge (FIGS. 4c & 4d). FIG. 4e shows cross sections of hemostatic sponges. FIG. 4f is a graph showing contact angle variation with time. This is a desirable feature in wound-healing systems as it can minimize the interaction of the foam sponge with the blood stream.

(2) Mechanical Properties

Figure 5:
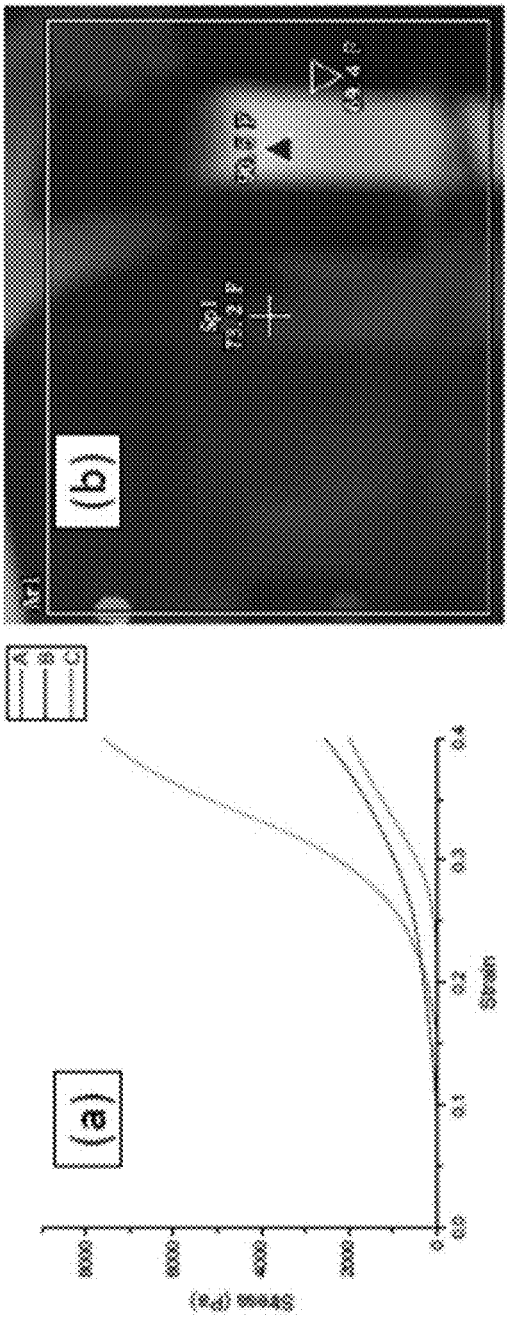
FIG. 5. (a) Compression test data comparison with different oxide-based foams; (b) thermal imaging and temperature control.

Compression test results have shown that the mechanical properties of the spongy polymeric matrix vary depending on the types of oxides used and their concentrations, thereby rendering such polymer-based foam sponges versatile hemostats for usage in different stress of injury (FIG. 5a).

Figure 6:
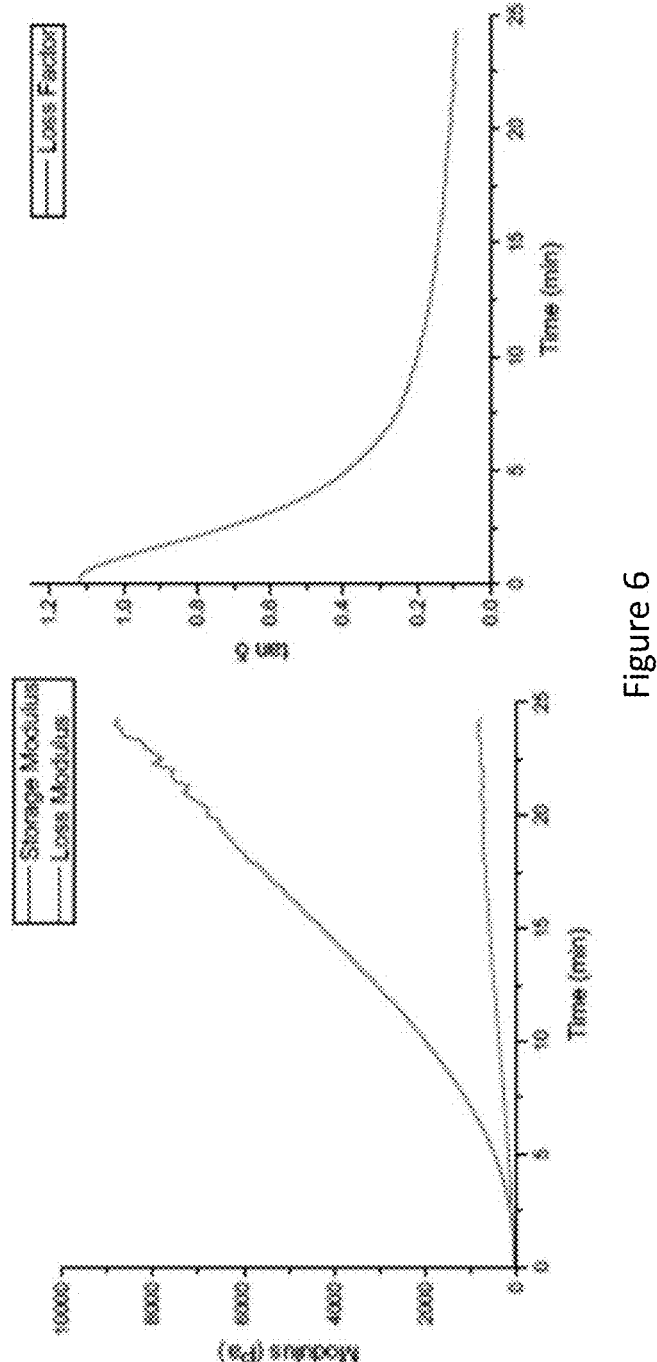
FIG. 6 shows characteristic viscoelastic behavior of the foam.

Further, from the viscoelastic tests, the liquid-to-foam point has been identified from the storage- and loss modulus curves (FIG. 6 and FIG. 7a).

The adhesive properties of the foam sponges render them optimal for wound dressing applications (FIG. 7b).

By tuning the relative concentrations of the respective oxides and $H_2O_2$, the temperature of the foaming reaction has been successfully controlled. The heat generated during the decomposition of $H_2O_2$ to $O_2$ and $H_2O$ serves two purposes. First, it acts to initiate and speed up the polymer curing of siloxanes, and secondly it decreases the viscosity of the first and second mixtures, facilitating easier combination. From the thermal analysis data, peak temperatures as low as 30° C./86° F. have been noted accompanied by a five-fold expansion (volume) in 20 seconds (FIG. 3d and FIG. 5b).

(3) Antibacterial Test

Since the polymer foam might contain Ag and oxygen trapped in lattice of polymers, antibacterial effect was expected. Antibacterial assays were conducted with gram-positive (*Staphylococcus aureus*) and gram-negative (*Escherichia coli*) bacteria by a disc diffusion method, and zones of inhibition of up to 15 mm were observed. (FIGS. 8a and 8b)

Figure 8:
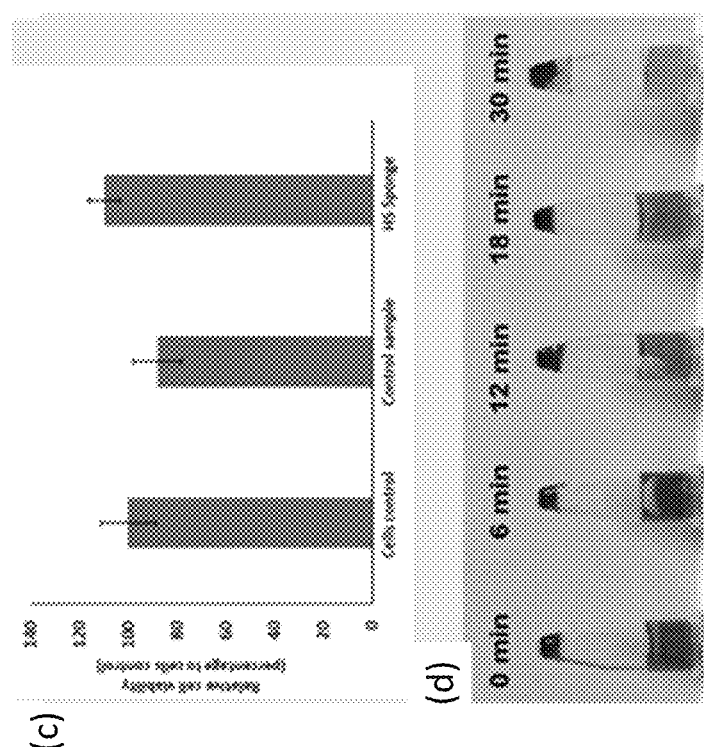
FIG. 8. Disc diffusion assay to measure antibacterial effect of hemostatic sponge (a) against *S. aureus* and (b) *E. coli*; (c) cytotoxicity assay, and (d) whole blood clotting assay.
Figure 8:
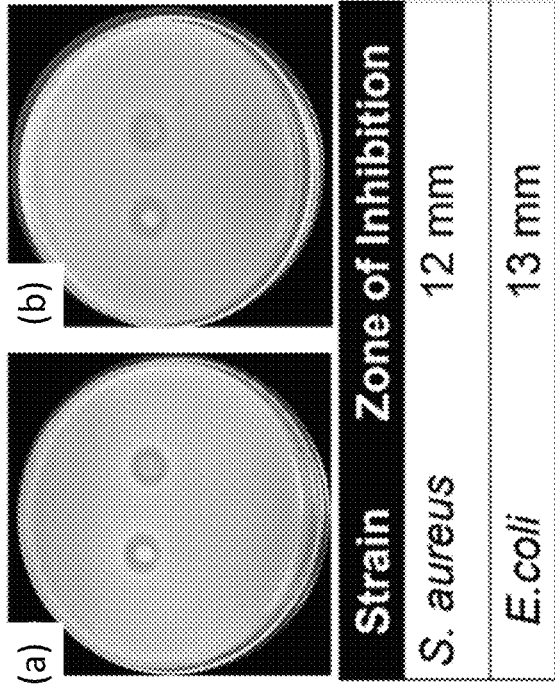

FIG. 8c shows the result of cytotoxicity assay. There is no significant difference between cell control without HS sponge and cells in the presence of HS sponge, indicating that HS sponge was proved non-cytotoxic.

FIG. 8d shows the result of whole blood clotting assay in the presence of HS-sponge. Usually, after collection of the whole blood, when the blood is allowed to clot by leaving it undisturbed at ambient temperature, blood clotting usually takes 15-30 minutes. The result demonstrates that HS-sponge does not affect blood clotting time, indicating that this synthetic sponge is biocompatible.

Figure 9:
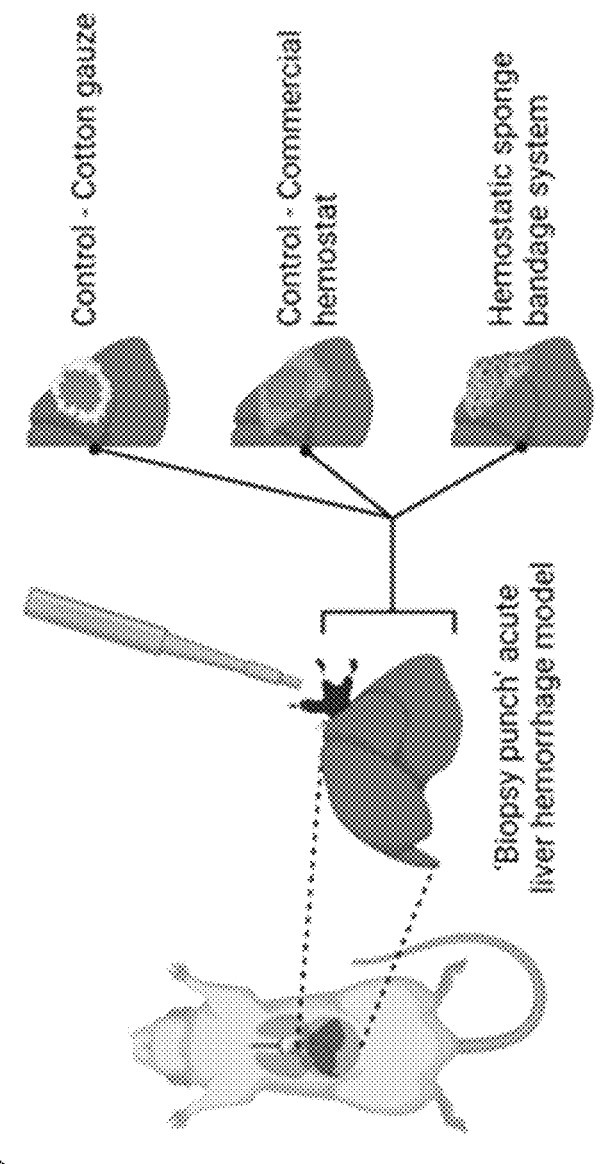
FIG. 9. A rat liver hemorrhage model for in vivo evaluation of hemostatic efficacy (IUPAC approval in process).

FIG. 9 is a rat liver hemorrhage model for in vivo evaluation of the hemostatic efficacy of the hemostatic bandage system disclosed here. Acute internal hemorrhage is induced by biopsy punch on the liver of a rat, and the efficacy of hemostatic materials was tested. As control, cotton gauze was used to stop bleeding. Then, commercial hemostat and the spongy-like foam produced using the inventive hemostatic bandage system were compared with each other and with control.

Conclusion: This unique strategy to develop a hemostatic dressing that contains oxygen-generating materials for supplying topical oxygen is a convenient approach for a biocompatible, hydrophobic, and antibacterial hemostatic bandage system that may find utility in treating different types of skin wounds, including pressure sores, ulcers, and recalcitrant open wounds. It can also be used under inclement weather conditions, which is often the case in the fields of operation.

REFERENCES

1. Ghimire, S.; Sarkar, P. et al. Pharmaceutics. 2021, 13, 2127.
2. Guo, B. et al. Nat. Rev. Chem. 2021, 5, 773.

What is claimed is:

1. A portable hemostatic bandage system comprising two formulations to form a polymer foam as in situ wound dressing at ambient temperatures for the control of mild, moderate, and severe hemorrhage, the portable hemostatic bandage system comprising:
   i) a first formulation comprising at least one type of polymer, at least one surfactant, at least one inorganic oxide or organic oxide or organic anhydride, and at least one polymer curing catalyst, wherein the at least one type of polymer in the first formulation comprises poly(dimethylsiloxane) (PDMS) and poly(dimethylsiloxane)-poly(ethylene oxide (PDMS-PEO);
   ii) a second formulation comprising at least one type of polymer at least one surfactant, hydrogen peroxide, and optionally, an aggregate; and
   ii) a dual container device having two separate chambers for keeping the two formulations separately, mixing the two formulations, and applying the resultant sponge-like polymer foam to the bleeding wound;
   wherein the polymer(s) in the second formulation can be at least one selected from siloxanes, functional siloxanes, vinyl terminated polymers, polyurethanes, polyacrylates, polymethylmethacrylates, epoxies, copolymers thereof, or mixture thereof,
   wherein the polymer(s) in the first and second formulations can be the same type of polymer or polymer mixture, or the polymer or the polymer mixture in the first formulation can be different from the polymer or polymer mixture in the second formulation, and
   wherein the first and second formulations are sterilized before packed into the separate chambers of the dual container device.

2. The portable hemostatic bandage system of claim 1 wherein the content ratio of PDMS and PDMS-PEO is 1:0.1 to 1:10, and wherein the total content of the polymers in the first formulation is about 0.1-100%, by weight or volume of the first formulation.

3. The portable hemostatic bandage system of claim 1, wherein the polymer in the second formulation is a siloxane.

4. The portable hemostatic bandage system of claim 3, wherein the polymer in the second formulation is poly (dimethylsiloxane) (PDMS).

5. The portable hemostatic bandage system of claim 3, wherein the content of the polymer in the second formulation is about 0.01-100%, by weight or volume of the second formulation.

6. The portable hemostatic bandage system of claim 1, wherein the surfactant can be anionic, cationic, amphoteric, Gemini, non-ionic, organic, inorganic, or combination thereof, and in particular non-ionic organic, and wherein the surfactant(s) in first formulation and second formulation can be the same surfactant(s), or the surfactant(s) in the first formulation can be different from that/those in the second formulation.

7. The portable hemostatic bandage system of claim 6, wherein the surfactant is at least one selected from polyoxyethylene sorbitan monolaurate, polyoxyethylene sorbitan monopalmitate, polyoxythylene sorbitan monostearate, polyoxyethylene sorbitan monooleate, and polyoxyethylene (10) iso-octylcyclohexyl ether, polyethylene glycol tert-octylphenyl ether, other poly(ethylene oxide)-based surfactants, polyoxyethylenated alkylphenols, polyoxyethylenated alcohols, monoglycerides of long-chain fatty acids, and the like.

8. The portable hemostatic bandage system of claim 6, wherein the surfactant in the first formulation and second formulation is non-ionic organic.

9. The portable hemostatic bandage system of claim 6, wherein the content of the surfactant in the first formulation is about 0.01-50%, by weight or volume of the first formulation.

10. The portable hemostatic bandage system of claim 6, wherein the content of the surfactant in the second formulation is about 0.001-50%; by weight or volume of the second formulation.

11. The portable hemostatic bandage system of claim 1, wherein the polymer curing catalyst is at least one selected from platinum (Pt), tin (Sn), titanium (Ti), zirconium (Zr), calcium (Ca), zinc (Zn)-compounds, complexes, or salts, and in particular Pt-compounds, complexes, or salts.

12. The portable hemostatic bandage system of claim 11, wherein the polymer curing catalyst is a Pt-divinyl siloxane.

13. The portable hemostatic bandage system of claim 11, wherein the content of the catalyst is about 0.001-50%, by weight or volume of one formulation.

14. The portable hemostatic bandage system of claim 1, wherein the aggregate is at least one selected from silica, fumed silica, zeolite, basalt, felspar, clay, aluminosilicates, mesoporous materials.

15. The portable hemostatic bandage system of claim 14, wherein the content of aggregate is about 0.001-50%, by weight or volume of the second formulation.

16. The portable hemostatic bandage system of claim 1, wherein the inorganic oxide is selected from CaO, MgO and $Ag_2O$.

17. The portable hemostatic bandage system of claim 16, wherein the content of the inorganic oxide is about 0.01% to about 70% by weight or volume of the first formulation.

18. The portable hemostatic bandage system of claim 1, wherein the first formulation and/or the second formulation optionally comprises painkillers, antibacterial and/or anti-fungal agents, antibodies, and/or any other bioactive agents to further complement hemostatic and regenerative action of the patient.

19. The portable hemostatic bandage system of claim 1, wherein the dual container device has:
   (i) two separate chambers that can keep the two formulations separated from each other;
   (ii) a common exit tip space of funnel shape, to which the two separate chambers open through a hole, wherein the diameter of the open hole is 0.001-15 mm;
   (iii) a common exit tip of syringe needle-like narrow open cylinder shape, which is connected to the common exit tip space, wherein the length of the tip is 1-300 mm, and the diameter of the tip is 0.01-100 mm; and
   (iv) a common force applier, plunger or squeezer, at one end of the chambers opposite to the end of common exit tip, in order to force the formulations in the separate chambers simultaneously into the common exit tip space, common exit tip, and wound site;

wherein the device is UV-irradiated before packed with the two formulations.

20. The portable hemostatic bandage system of claim 19, wherein the dual container device has a plurality of turbulators dispersed inside the common exit tip space in a helical arrangement so that the mixtures passing through the tip are stirred and agitated to be mixed.

21. The portable hemostatic bandage system of claim 19, wherein the dual container device can be a turbulator-dispersed dual-syringe applicator having one common plunger for the two chambers containing the first formulation and second formulation formulations sealed inside, respectively.

\* \* \* \* \*